United States Patent
Mok et al.

(10) Patent No.: US 6,643,541 B2
(45) Date of Patent: Nov. 4, 2003

(54) WIRELESS ELECTROMYOGRAPHY SENSOR AND SYSTEM

(75) Inventors: Swee Mok, Schaumburg, IL (US); Di-An Hong, Barrington, IL (US); Thomas S. Babin, Lake Zurich, IL (US); Sanjar Ghaem, Chesapeake, VA (US)

(73) Assignee: Motorola, Inc, Schaumburg, IL (US)

( * ) Notice: Subject to any disclaimer, the term of this patent is extended or adjusted under 35 U.S.C. 154(b) by 0 days.

(21) Appl. No.: 10/008,720

(22) Filed: Dec. 7, 2001

(65) Prior Publication Data

US 2003/0109905 A1 Jun. 12, 2003

(51) Int. Cl.[7] ............................................. A61B 5/0488
(52) U.S. Cl. ........................ 600/546; 600/391; 128/903
(58) Field of Search ................................ 600/393, 391, 600/392, 546, 509; 128/903

(56) References Cited

U.S. PATENT DOCUMENTS

| 4,121,573 | A | * | 10/1978 | Crovella et al. | ............ | 128/903 |
|---|---|---|---|---|---|---|
| 4,448,203 | A | | 5/1984 | Williamson et al. | | |
| 5,168,874 | A | | 12/1992 | Segalowitz | | |
| 5,203,330 | A | | 4/1993 | Schaefer et al. | | |
| 5,511,553 | A | * | 4/1996 | Segalowitz | ................. | 128/903 |
| 5,579,781 | A | | 12/1996 | Cooke | | |
| 6,161,036 | A | * | 12/2000 | Matsumura et al. | ........ | 128/903 |
| 6,238,338 | B1 | * | 5/2001 | DeLuca et al. | ............. | 128/903 |
| 6,285,899 | B1 | * | 9/2001 | Ghaem et al. | .............. | 128/903 |

* cited by examiner

*Primary Examiner*—George R. Evanisko
(74) *Attorney, Agent, or Firm*—Daniel K. Nichols

(57) ABSTRACT

A wireless biopotential sensor includes an adhesive strip having a lower surface for placement against the skin of a patient and an upper surface. A pair of conductive electrodes are applied to the lower surface of the adhesive strip. A sensor substrate is applied to the upper surface. The sensor substrate includes first and second conductive contact pads that are placed in registry with the pair of conductive electrodes, with the contact pads arranged in electrical contact with the conductive electrodes. An electronics module is applied to the sensor substrate and arranged in electrical contact with the contact pads. The electronics module comprises a power supply and electronics for generating a wireless signal containing biopotential signals detected by the pair of conductive electrodes.

8 Claims, 7 Drawing Sheets

WIRELESS ELECTROMYOGRAPHY SENSOR AND SYSTEM

CROSS-REFERENCE TO RELATED APPLICATION

This relates to application Ser. No. 09/551,718 and application Ser. No. 09/551,719, both filed on filed Apr. 18, 2000, the contents of both are incorporated herein by reference.

BACKGROUND OF THE INVENTION

A. Field of the Invention

This invention relates generally to the field of devices used to measure and display bio-potential signals generated by the body. More particularly, the invention relates to a wireless, remotely programmable electrode transceiver assembly that sends electromyography (EMG) signals via wireless transmission to a base unit. The base unit obtains a patient's EMG signal from the wireless transceiver and supplies the signal to a monitor unit for display.

B. Statement of Related Art

Electromyography is technique by which electrical activity associated with functioning skeletal muscle is converted to a perceptible, usually visual, record. The technique is used to help diagnose certain neuromuscular disorders, such as Parkinson's disease, and in biofeedback training.

EMG equipment has heretofore typically taken the form of one or more electrodes that are attached to the patient's skin adjacent to the skeletal muscle of interest, an EMG display monitor, and a set of wires connecting the electrodes to the monitor. Some tests, such as Parkinson disease tests, can require more than 10 sensors, each with four wire lines. The wires coupling the electrodes to the monitor limit patient mobility, increase the amount of time needed to set the patient up for the EMG acquisition, and can restrict or prevent the patient from engaging in many types of motions or exercises during the acquisition of the EMG signal (e.g., walking, running, rowing machine, etc.).

Wireless medical monitoring and diagnosis systems have been proposed in the prior art. U.S. Pat. No. 5,862,803 to Besson et al. describes a wireless electrode/sensor patch system with sensor, controller and transceiver electronics contained in an electrode patch assembly. U.S. Pat. Nos. 5,307,818, 5,168,814 and 4,981,141, all issued to Segalowitz, describe a wireless electrode system for electrocardiogram (ECG) monitoring. The Besson et al. and Segalowitz patents are incorporated by reference herein.

The Segalowitz patents describe a single piece electrode patch with built-in microchips for wireless one way communication and a snap on electronic-assembly that fastens to a disposable electrode patch. However, the electrode patch is a special two-conductor type that is not conventional. The electrode assemblies are either transmit only or receive only (not both). A reference signal is transmitted from the base unit to only the Right Leg electrode patch, which is receive only. Electrodes can only be programmed via manual switches on the electrode casing, not over-the-air from the base unit. For the multiple electrode embodiment, the base unit contains multiple receivers and antennas which imply multiple transmit frequencies are required for the system and over-the-air signaling (thus making the base unit more costly to implement). There is no mention of error correction or detection capability in the electrodes or base unit.

In another embodiment of the Segalowitz '818 patent, there is discussion of a single strip assembly which contains all of the electrodes required for 12-lead ECG monitoring with microchip circuitry contained in the strip assembly (not in the individual electrode patches). In this configuration, the ECG signals from each electrode are multiplexed and transmitted from a single transmitter contained in the strip assembly via time multiplexing on a single digitally encoded frequency channel. However, no time multiplexing on a single frequency channel is discussed for their multiple transmit electrode embodiment.

The present invention provides a self-contained device that can acquire an EMG signal, in the form of voltage level, from the surface of the skin. The EMG signal is digitized and sent to a base station using wireless technology. Multiple wireless EMG signals in accordance with the invention can be used on the patient, such as in a 10 electrode Parkinson disease EMG test. Because the system is a wireless system, the problems enumerated above associated with wires leading from the electrode to the monitor are avoided.

SUMMARY OF THE INVENTION

A wireless biopotential sensor includes an adhesive strip having a lower surface for placement against the skin of a patient and an upper surface. A pair of conductive electrodes are applied to the lower surface of the adhesive strip. A sensor substrate is applied to the upper surface. The sensor substrate includes first and second conductive contact pads that are placed in registry with the pair of conductive electrodes, with the contact pads arranged in electrical contact with the conductive electrodes. An electronics module is applied to the sensor substrate and arranged in electrical contact with the contact pads. The electronics module comprises a power supply and electronics for generating a wireless signal containing biopotential signals detected by the pair of conductive electrodes.

In another aspect, a wireless electromyography acquisition system is provided. The system includes a plurality of individual, remotely programmable sensors each having a wireless transceiver. Each of the sensors includes a patch electrode adapted to be placed on the surface of the patient's body for measuring electrical potentials from skeletal muscle. The system further includes a base unit comprising a wireless transceiver for sending and receiving messages to the plurality of individual wireless transceivers. The electrodes include circuitry for converting received EMG signals into digital form.

Each of the wireless electrodes includes a means for encoding unique identification information associated with the wireless electrodes, such as manufacturer serial number and user-selected identification codes. An analog to digital converter and microcontroller computing platform are included in the sensor and provide a means for converting the digital form of the EMG signals into packets and for appending the encoded identification information to the packets. A buffer is provided for storing EMG digital data containing the encoded identification information prior to transmission by the electrode's transceiver to the base unit.

Time division multiplexing is a preferred way by which the multiple EMG electrodes transmit wireless data to the base unit. The base unit transmits a global time base signal to the individual wireless transceivers. The global time base signal is used for synchronizing the timing of transmission of signals acquired by the individual wireless electrodes to the base unit in discrete time slots in a single frequency channel. This time division multiplexing provides that each wireless transceiver transmits its signals to the base unit in discrete time slots, with the wireless transceivers sharing a common channel.

The base unit has an interface to an EMG monitor for display and analysis by the user. Preferably, the EMG monitor is a conventional, standard monitor typically used today in the hospital setting. The EMG signals are provided by the base unit to the monitor in a fashion that is transparent to the monitor, i.e., the data is formatted and provided in a form whereby the monitor cannot distinguish the signals from conventional, wired electrode input signals.

These and still other aspects and features of the invention will be more apparent from the following detailed description of a presently preferred embodiment.

BRIEF DESCRIPTION OF THE DRAWINGS

A presently preferred embodiment of the invention is described below in conjunction with the appended drawing figures, wherein like reference numerals refer to like elements in the various views, and in which.

DETAILED DESCRIPTION OF THE PREFERRED EMBODIMENT

Figure 1:
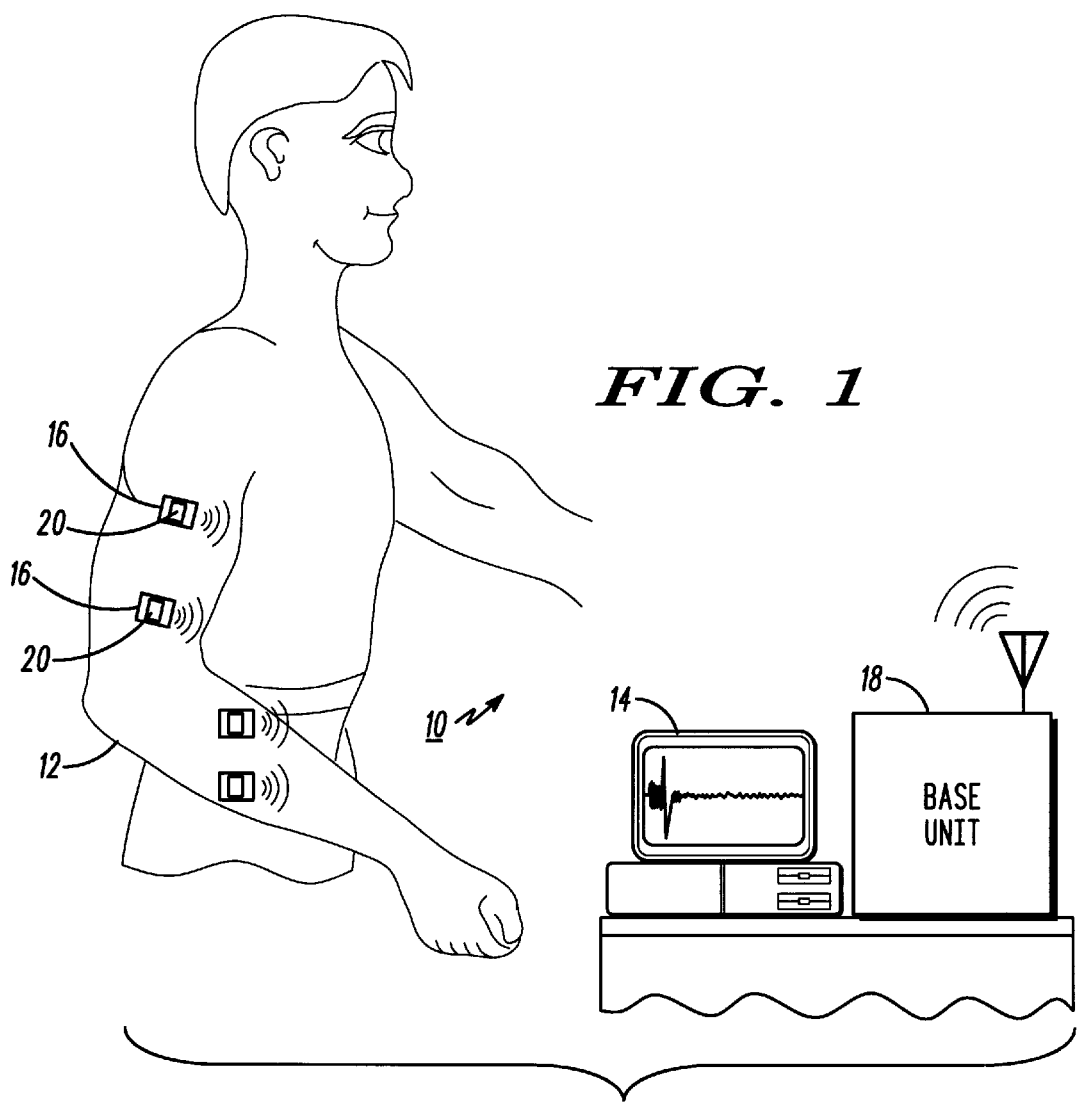
FIG. 1 is a schematic representation of the system of the present invention in use with a patient to acquire EMG signals from the patient and supply them to an EMG monitor.

In one aspect, and with reference to FIG. 1, the present invention provides a system 10 consisting of multiple smart wireless EMG sensors 16 for use with a patient 12 undergoing wireless EMG or other medical monitoring. The system also includes a base unit 18 communicating with the wireless sensors that also interfaces to existing conventional EMG monitoring and display equipment 14. The electrode devices receive commands from the base unit such as registration information, transmission frequency commands, amplifier gain commands, transmitter control commands, power saving mode, etc. and include hardware and software or firmware for processing these commands and responsively configuring the sensors accordingly.

To avoid interference from other wireless systems that may be in RF range of the base unit (such as in a hospital or clinic environment), time division multiplexing in a common or shared frequency channel is a preferred form by which the EMG data is transmitted from multiple sensors to the base unit. For example, in a Parkinson's disease wireless EMG embodiment, ten electrodes 16 are placed on the patient and transmit EMG data to the base unit in a single frequency channel, with the signals from the various sensors placed in discrete time slots. To facilitate synchronization among the various sensors, the sensors will also preferably receive a global time base signal from the base unit. The global time base signal is also used for in synchronizing the timing of acquisition of sample points for all electrodes used in measuring input body surface potentials (e.g., EMG signal).

The base unit 18 receives the transmitted EMG signal from each electrode (at predetermined time intervals if time division multiplexing is the embodiment of the communication protocol), demodulates, decodes (with error correction), digitally processes the data, applies any needed signal conditioning (amplification, filtering), and converts back to analog form for outputting the EMG signals to the standard EMG equipment 14 for display. The base unit also has a universal interface to existing standard EMG equipment so that the wireless link between the electrodes and base unit appears transparent to the EMG equipment. While time division multiplexing is a presently preferred embodiment for the transmission of EMG signals, other transmission formats could be used. An example of an alternative transmission format is code division multiplexing, a technique known in the wireless communications art.

The wireless sensors 16 and base unit 18 preferably use an over-the-air communication protocol between the base unit and the electrodes which allows wireless programming (configuration), identification, auditing, data acquisition control, and transmitter control of each electrode used in the EMG system. For frequency bandwidth efficiency of the invention, the system could be designed such that transmission of multi-channel EMG signals is on a single digitally encoded frequency channel between the base unit transceiver and multiple electrode devices by using time division multiplexing. For example, each electrode will receive synchronization data from the base unit on the same receive frequency, and instruction on which time slot to transmit it's digitally encoded EMG data. This makes it possible for multiple patients to use the wireless EMG system in the same hospital room if there is limited bandwidth.

The system 10 is a wireless system, in that a plurality of electrode assemblies 16 receive commands (e.g., synchronization and control commands) from a base unit 18 using wireless transmission methods, and supply the EMG signals to the base unit 18 using wireless transmission methods as well. Thus, cumbersome wires for the electrode assemblies 16 are eliminated in the illustrated embodiment.

Figure 2:
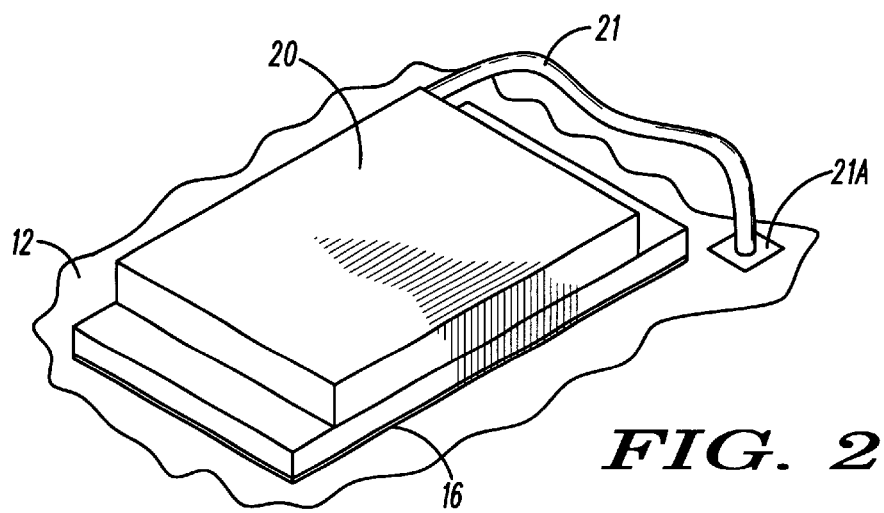
FIG. 2 is a detailed perspective view of one of the patch electrodes and associated remotely programmable wireless transceiver of FIG. 1, it being understood that all of such patch electrodes and wireless transceivers of FIG. 1 are of a construction similar to that shown in FIG. 2.
Figure 3:
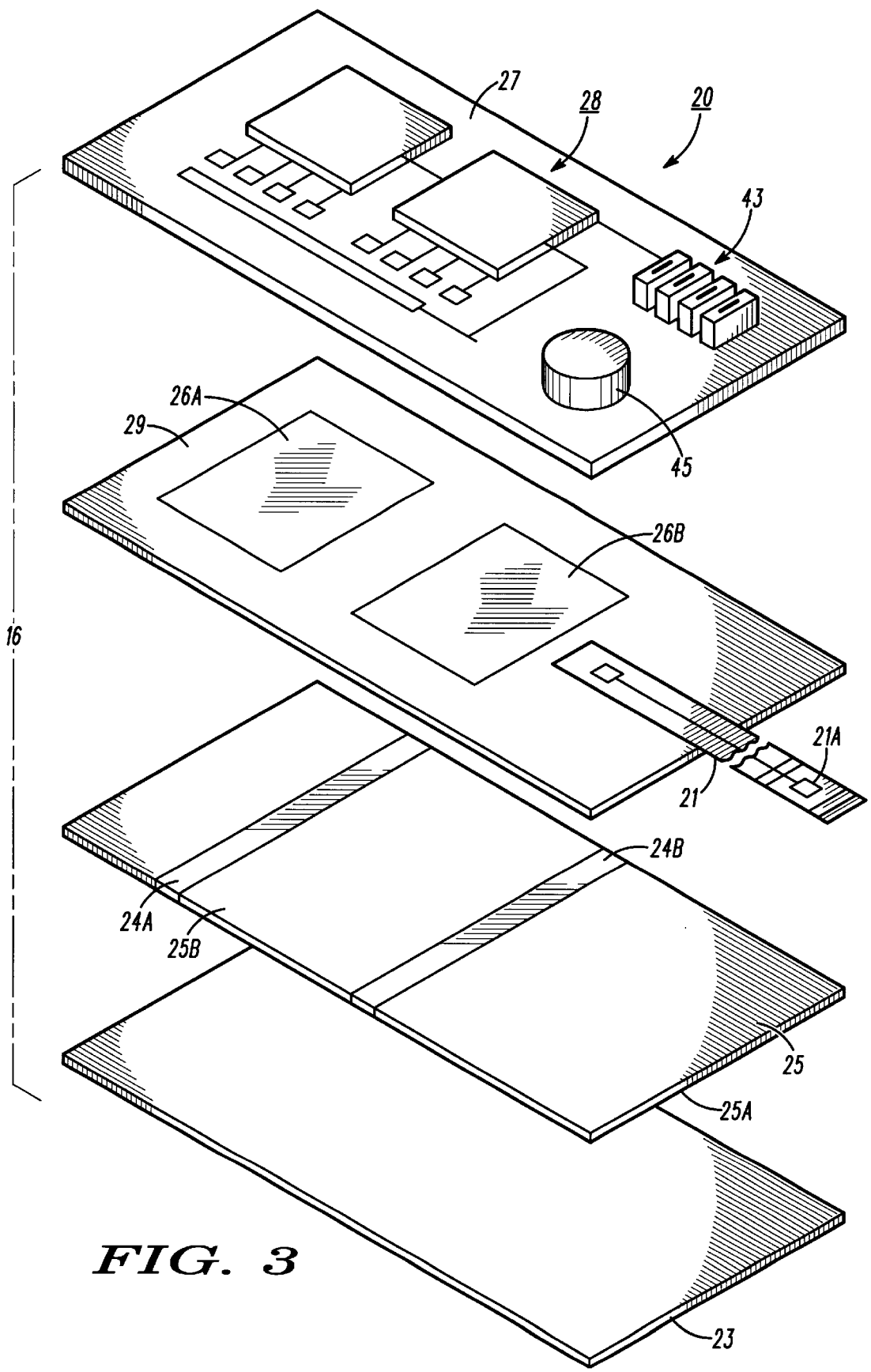
FIG. 3 is an exploded view of one wireless EMG sensor of FIG. 2, with the cover for the sensor removed.

The electrode assemblies 16 of FIG. 1 consist of a plurality of individual, remotely programmable wireless transceivers 20, each transceiver designed to mount to a patch electrode 16 shown in FIG. 3. The wireless transceivers are described in further detail in conjunction with FIGS. 2, 3 and 5. The base unit 18 includes a wireless transceiver for sending and receiving messages to the plurality of individual wireless transceivers, and is described in further detail in conjunction with FIGS. 9 and 10. The base unit further has an interface for providing analog EMG signals received from the wireless transceivers 20 to a conventional EMG display monitor 14.

The messages transmitted by the base unit 18 also include configuration commands for the wireless transceivers 20.

Figure 10:
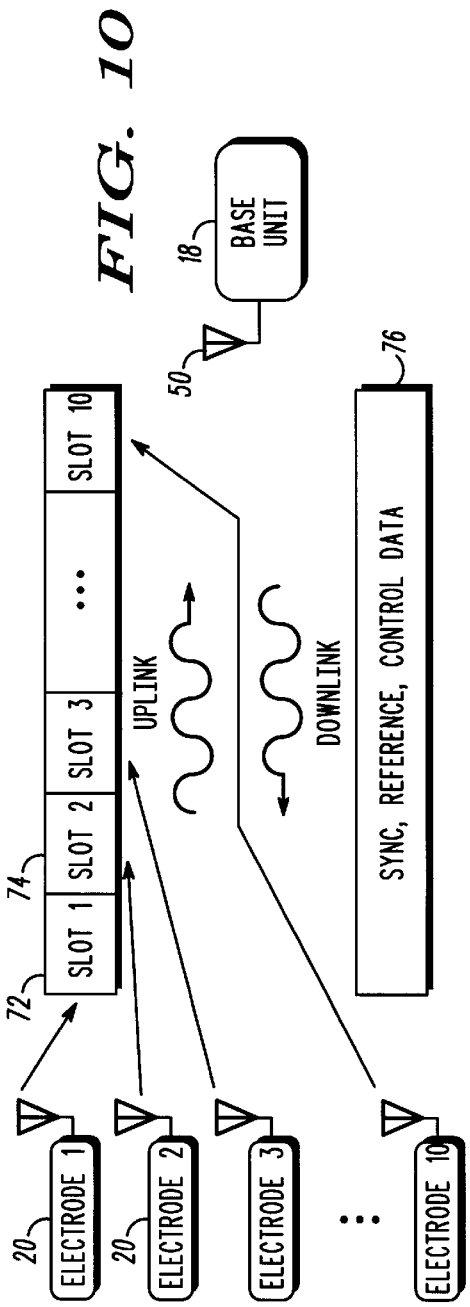
FIG. 10 is an illustration of time division multiplexing communications format used by the wireless transceivers in the EMG sensors of FIG. 1.

These configuration commands can be, for example, change or set the data acquisition sampling rate, amplifier gain setting, and channel carrier settings, and can also consist of a timing signal for synchronization of the transmission time slot. Preferably, the base unit 18 transmits a global time base signal to all of the wireless transceivers. The global time base signal synchronizes the timing of transmission of the EMG signals acquired by all of the wireless transceivers 20, such that the transmissions are in discrete time slots in a single frequency channel, as shown in FIG. 10 and described subsequently.

The details of the over-the-air programming protocol to exchange messages and information between the base unit and the transceivers may be arrived at in many ways within the spirit of the present invention, and is considered within the ability of a person skilled in the pertinent art. In one possible embodiment, packets of data are transmitted between the base unit and the wireless transceivers. Particular fields in the packets (bytes of data) are reserved for control data, payload data, CRC or error correction data, etc. in accordance with known wireless transmission protocols, conventional data transmission techniques such as IP or Ethernet, or similar techniques. A presently preferred protocol is described in the application of Mohammad Khair et. al., Ser. No. 09/551,718 and Ser. No. 09/551,719 both filed Apr. 18, 2000, the contents of which are incorporated by reference herein.

FIG. 2 is a detailed perspective view of one of the patch electrodes 16 and associated remotely programmable wireless transceiver 20 assembly of FIG. 1, it being understood that all of such patch electrodes and wireless transceivers of FIG. 1 are of a construction similar to that shown in FIG. 2. The patch electrode 16 is adhered to the surface of the patient's body 12 in conventional fashion. A local ground reference is provided consisting of a flexible strip 21 connected to the transceiver 20 having a tip or skin contact 21A, made from a conductive material, which is placed adjacent to the patch electrode 16 in contact with the skin. The purpose is to allow the transceiver to measure the biopotential difference between the signal contact points in the electrodes and the local ground reference 21A. The material used for the strip 21 could be a thin flexible material such as plastic with an internal conductive trace or lead wire from the transceiver 20 to the skin contact point 21A.

Figure 4:
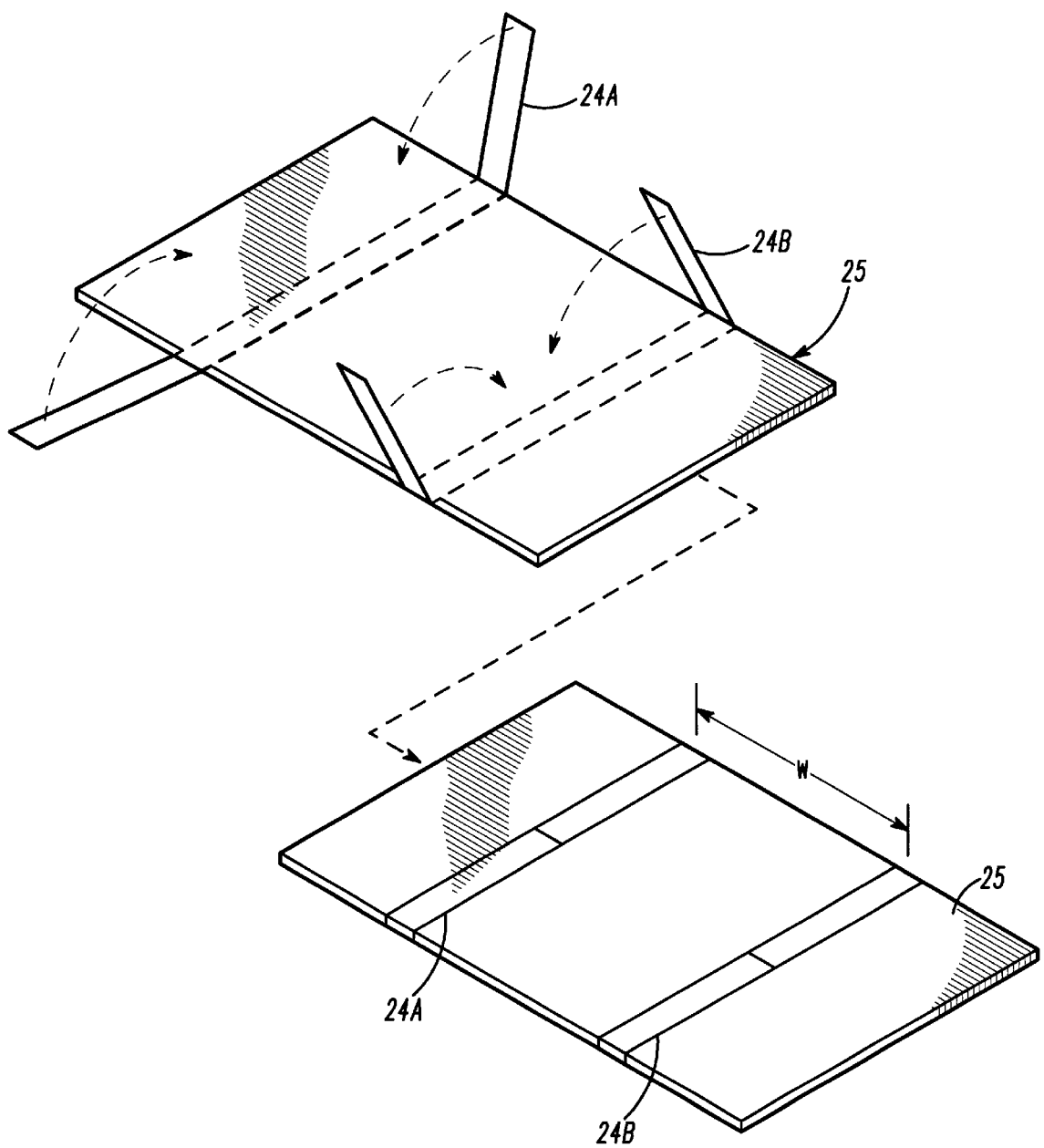
FIG. 4 is a perspective view of the adjustable electrode strip of FIG. 3, showing how the conductive strips are folded onto the insulative substrate.

FIG. 3 is an exploded view of the electrode assembly 16. The assembly includes a flexible protective adhesive tape 23 that is removed when the electrode is applied to the patient, exposing an adhesive strip 25. An adhesive is applied to both sides of the strip 25. The strip has a lower surface 25A for placement against the skin of a patient and an upper surface 25B. A pair of conductive electrodes 24A and 24B are applied to the adhesive strip. One of the electrodes 24 is designated as a–electrode and the other is designated as the + electrode. FIG. 4 shows how the thin strips of conductive material forming the electrodes 24 are folded onto the adhesive substrate 25, and separated from each other by a predetermined width W. The width W is adjustable by removing and re-applying the electrodes 24. This feature allows the user to reposition the electrodes on the substrate 25 to get better signal collection or signal to noise ratio in the acquired EMG signal potentials.

A sensor substrate 29 is applied to the upper surface 25B of the adhesive strip 25. The sensor substrate 29 carries first and second conductive contact pads 26A and 26B placed in registry with the pair of conductive electrodes 24A and 24B, such that the contact pads 26A and 26B are in electrical contact with the conductive electrodes 24A and 24B when the unit is assembled. The conducting pads provide a means to couple the acquired EMG signals to the signal electronics 28 on the substrate 27 above strip 25.

The sensor substrate 29 also includes the reference strip 21 carrying a conductor leading to the reference electrode or skin contact portion 21A.

A wireless transceiver and electronics module indicated generally at 20 is applied to the sensor substrate 29 in electrical contact with the contact pads 26A and 26B. The electronics module comprises a power supply 45 and electronics 28 for generating a wireless signal containing biopotential signals detected by the pair of conductive electrodes 24A and 24B. The electronics 28 are mounted to a substrate 27. The electronics includes a four position identification number selector DIP switch 43, which are used to assign unique identification number to each electrode, e.g., based on the functional position or location where the electrode is attached to the patient. This is necessary for the base unit to correctly correlate the received EMG signals to the proper position on the patient. The four position DIP switch 43 allows for 15 different wireless EMG sensors to be used on a patient. Position 0 shuts off the sensor. Positions 1–15 are recognized as ID numbers for encoding each sensor's data. To increase the number of ID selections available, a DIP switch with more switching positions can of course be used.

Figure 5:
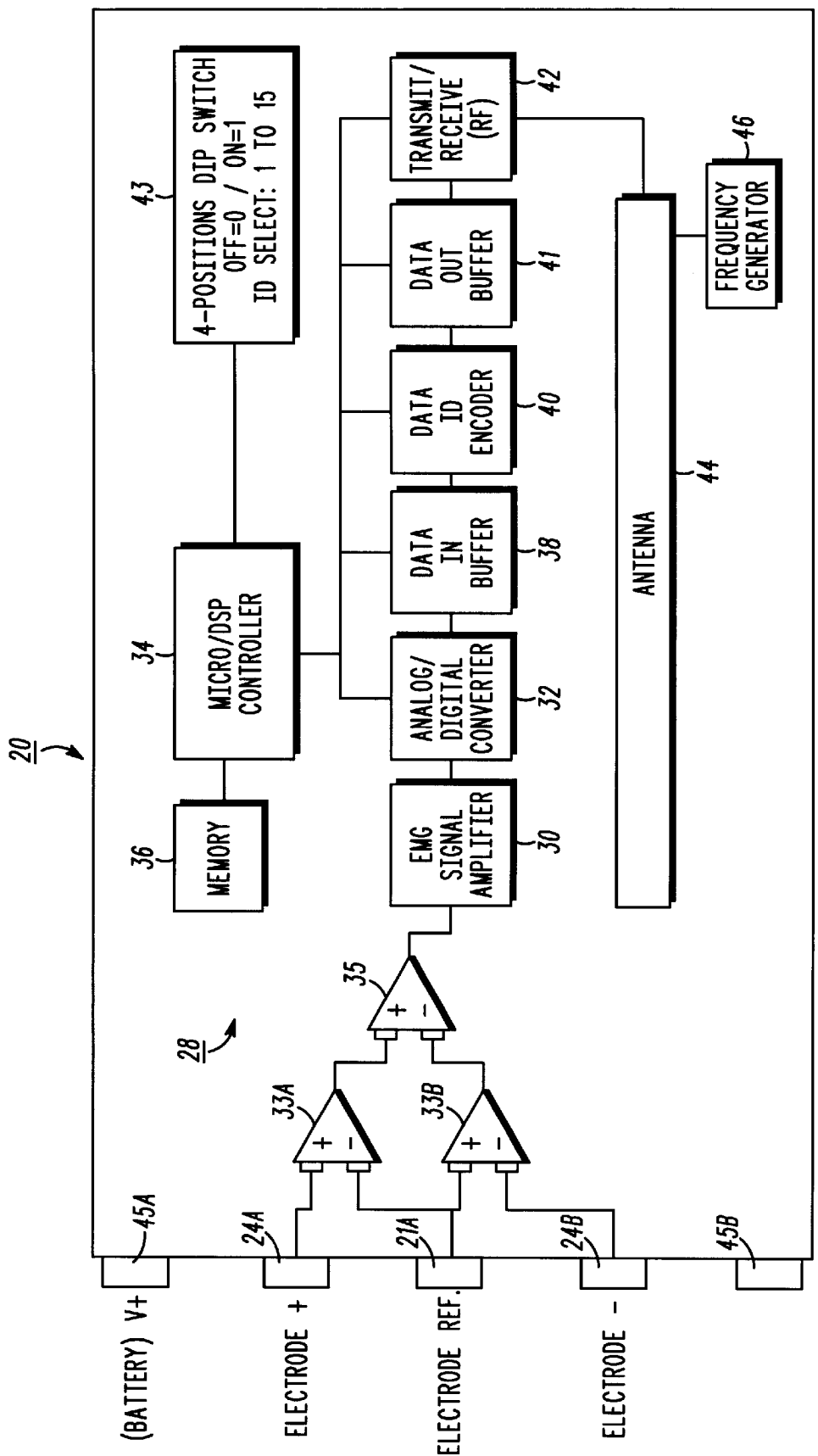
FIG. 5 is a block diagram of the electronic circuitry of the wireless EMG sensor of FIG. 3.

The electronics 28 of the wireless transceiver module 20 is shown in a block diagram form in FIG. 5. A battery 45 (FIG. 3) with + and − terminals 45A and 45B provides DC power to the components. The + and −electrodes 24A and 24B of FIG. 3 supply voltages to + and − terminals of pre-amplifiers 33A and 33B, respectively. The reference electrode 21A supplies a voltage to the − and + terminals of the pre-amplifiers 33A and 33B, respectively. Output voltage signals from the amplifiers 33A and 33B are supplied to a second stage amplifier 35 and sent to a low noise, variable gain EMG signal amplifier 30. The analog signal from amplifier 30 is filtered, sampled and converted to digital signals in the A/D converter 32. The digital signals are supplied to a computing platform, illustrated as a microcontroller/Digital Signal Processor 34. The microcontroller performs signal processing of the digital signal supplied by the A/D converter 32. The signal processing functions include noise filtering and gain control of the digital EMG signal. In an alternative but less-preferred embodiment, gain control in the transceiver assembly could be performed by adjustment of the amplifier 30 gain in the analog signal path. The microcontroller also processes commands and messages received from the base unit, and executes firmware instructions stored in a memory 36. The memory further stores a unique electrode identifier as described in further detail below. The memory may also store a position location identifier or data associated with a position the electrode is attached to the patient, programmed dynamically via the four position DIP switch 43. The position location identifier or data could also be dynamically programmable from the base unit.

The processed digital EMG signals are buffered in a buffer 38 and supplied to an encoder 40. Encoded EMG signal and Identification data is stored in a data out buffer 41 and fed to a RF transceiver module 42 for transmission to the base unit via a low power built-in RF antenna 44. The transceiver 42 includes a modulator/demodulator, transmitter, power amp, receiver, filters and an antenna switch. A frequency generator 46 generates a carrier frequency for the RF transmission. The frequency is adjustable by the microcontroller 34. The microcontroller/DSP 34 controls the frequency generator 46 so as to select a frequency for wireless transmission of data and control messages to the base unit. The microcontroller in the computing platform 34 also executes an initialization routine wherein the receiver scans a default receive channel for commands from the base unit, and if the commands are received the transmitter transmits identification information in an assigned frequency and time slot to the base unit.

All or some of the individual blocks shown in FIG. 5 could be combined in a microchip or microchips to miniaturize the size of the snap-on wireless transceiver assembly 20.

Figure 6:
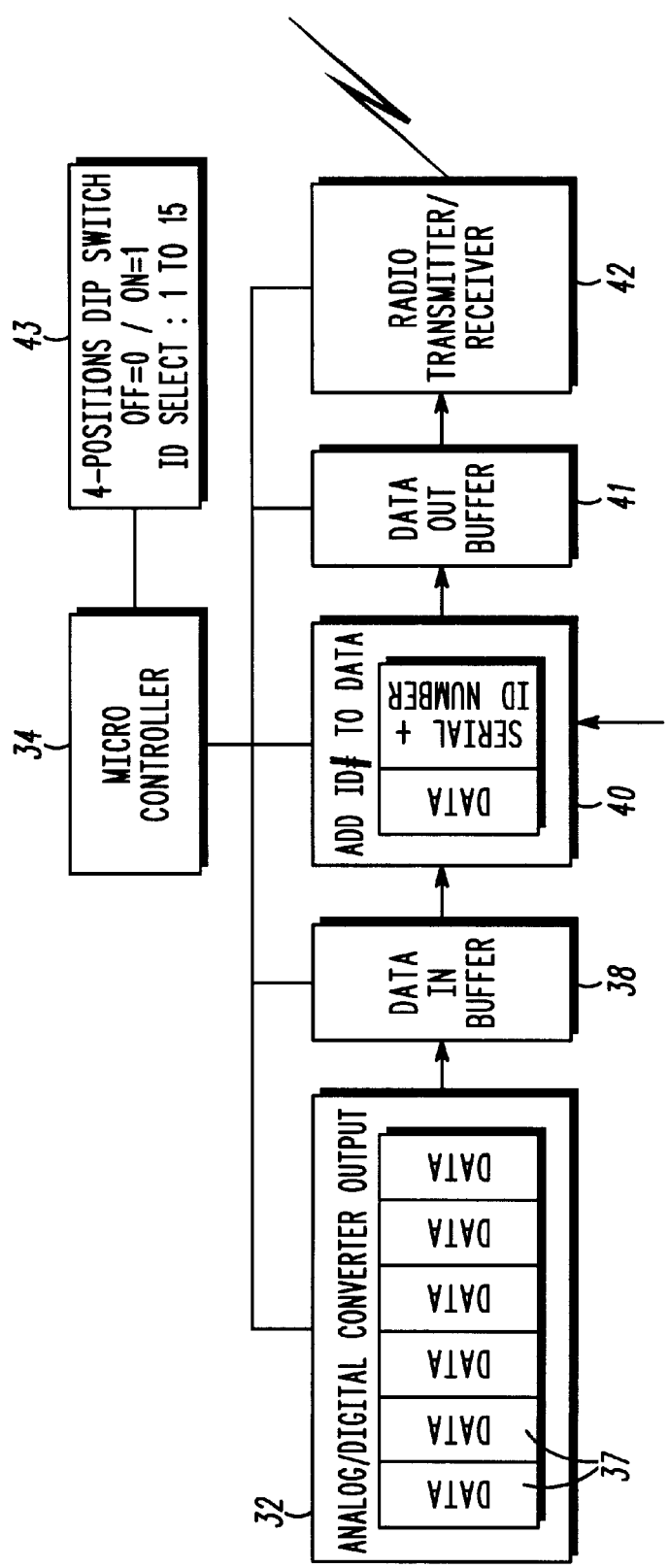
FIG. 6 is a more detailed illustration of the circuitry of FIG. 5 showing the digitization of EMG data and grouping into packets of data, the data being combined with an identification number prior to transmission.

FIG. 6 is a more detailed block diagram of a portion of the electronics of FIG. 5, showing the blocks of digitized EMG data being combined with the electrode serial number and identification number in the data IN encoder 40, before radio transmission 42. Each packet of data sent by the wireless EMG sensor has a serial number plus ID number as part of its data header. The serial number plus ID number can also be used to encode packet data, select a radio frequency, and Internet Protocol (IP) address, or be used in other data encoding schemes such as CDMA.

Figure 7:
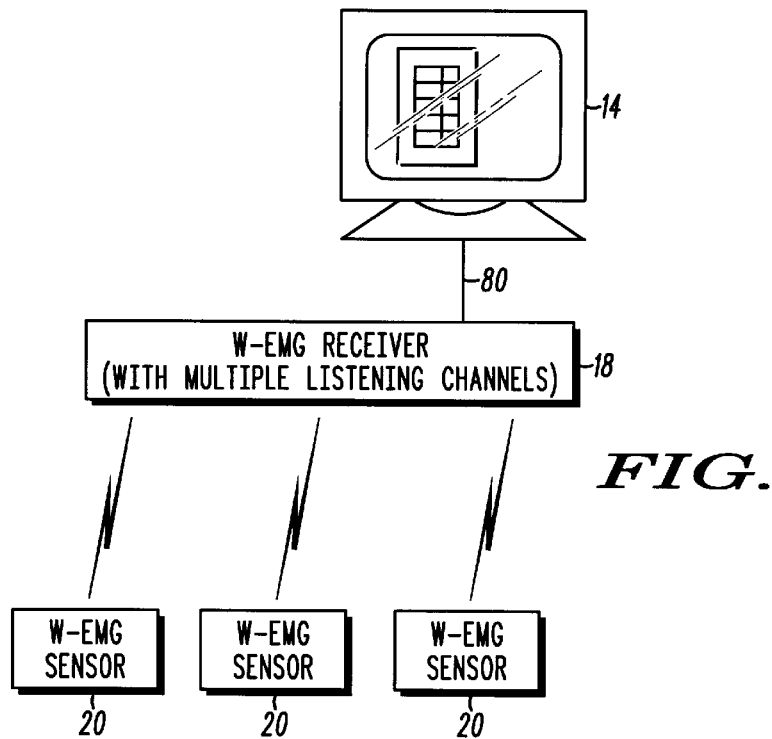
FIG. 7 is an illustration of a multiple channel receiver system for a plurality of wireless EMG sensors.
Figure 8:
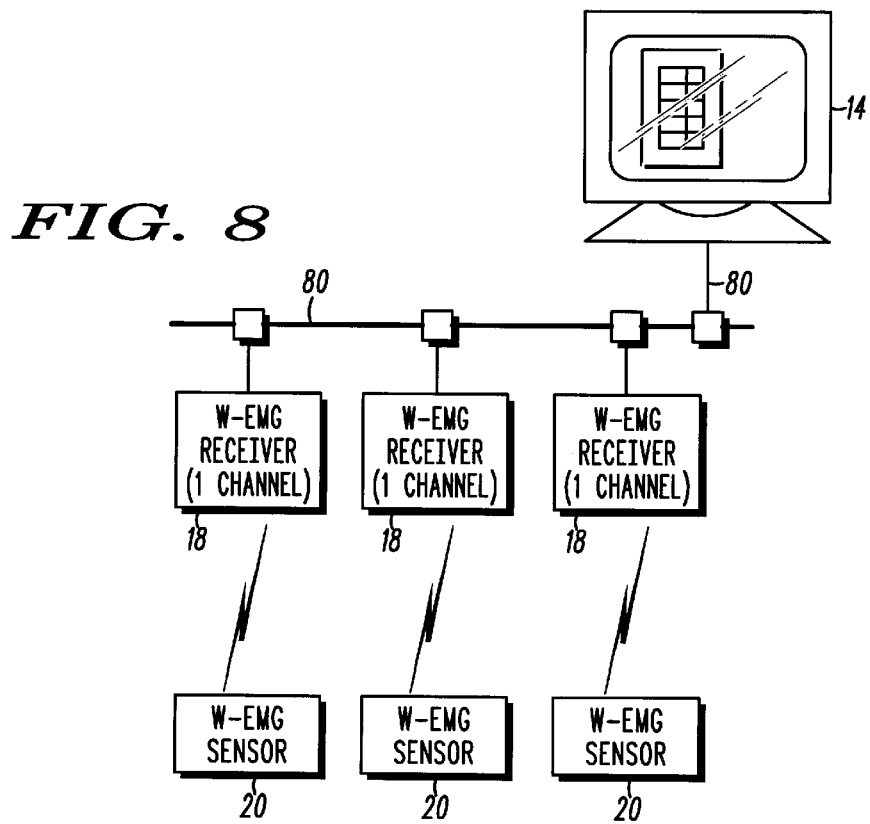
FIG. 8 is an illustration of a distributed receiver system for a plurality of wireless EMG sensors.

FIG. 7 is an illustration of a multiple channels receiver system in which a plurality of wireless EMG sensors 16 transmit over multiple frequency channels to a wireless EMG receiver or base unit 18. The base unit supplies the EMG data to an EMG analysis workstation for display or analysis. FIG. 8 shows an embodiment in which the wireless receivers are located on a local area network 80. Each wireless EMG sensor 16 has its own uniquely assigned channel, and transmits to its assigned receiver or base unit 18. The data from the EMG sensors is sent over the network 80 to the workstation 14 for display or analysis.

By providing each wireless electrode sensor with its own sensor serial number and a user-selected ID number programmed via the four-position DIP switch 43 (FIG. 3), a number of advantages are obtained. First, this arrangement allows multiple wireless EMG sensors to be used simultaneously in close proximity, without interference or cross talk between the different sensors. Sensor signal interference from another wireless EMG system, for example a sensor used in the next room in the hospital using the same frequency, can be recognized in the base unit and corrective action can be taken. For example, the base unit could command the affected sensor experiencing interference to change its channel. Further, the sensor serial number and ID selector number can be interpreted as a network plus computer number in an Internet-like addressing scheme, which gives some additional flexibility to the handling of the EMG data over the networks shown in FIGS. 7 and 8.

Figure 9:
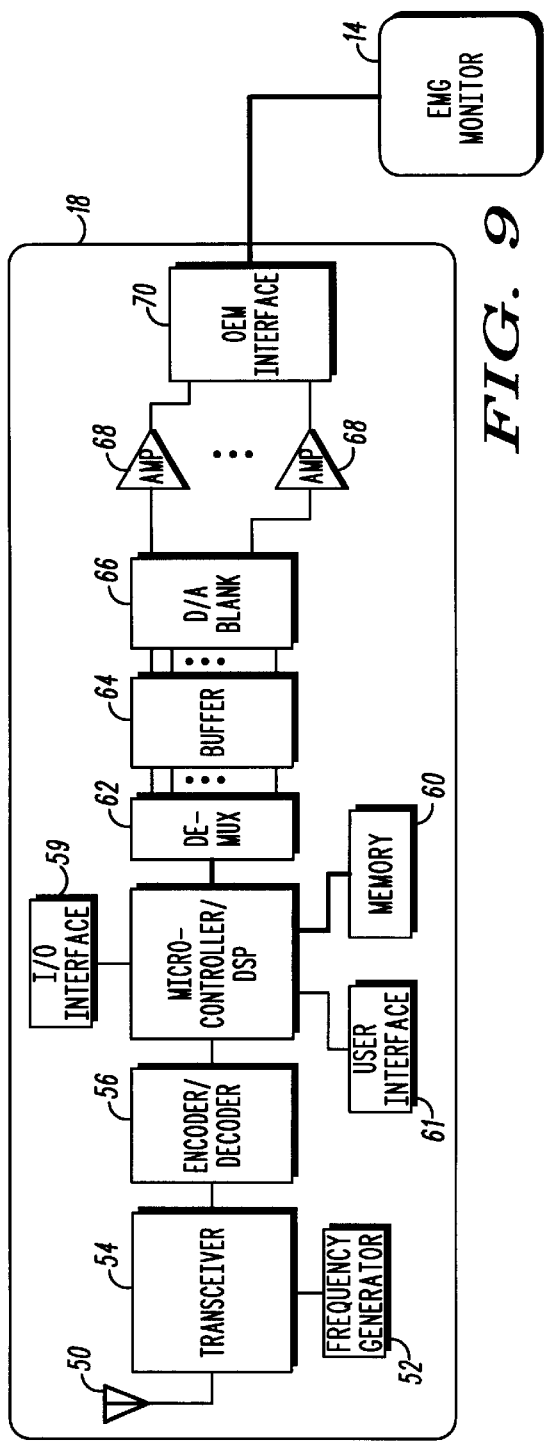
FIG. 9 is a block diagram of the base unit of FIG. 1.

Referring now to FIG. 9, one possible embodiment of a base unit 18 is shown in block diagram form. The base unit 18 transmits commands to all of the wireless transceivers and instructs each transceiver to transmit its EMG data individually (such as in time division multiplexing). The base unit receives the transmitted EMG signals from the electrodes (up to 10) in sequence and then demodulates, decodes, error corrects, de-multiplexes, buffers, signal conditions, and reconverts each electrode's data back to an analog signal for interfacing to the standard EMG monitor 14. The base unit also transmits programming information to the electrodes for frequency selection, power control, etc.

The base unit 18 includes a low power RF antenna 50, a frequency generator 52 for generating a carrier frequency and an RF transceiver 54. The transceiver 54 includes a modulator/demodulator, transmitter, power amp, receiver, filters and an antenna switch. The base unit further includes a encoder/decoder 56, a computing platform such as a microcontroller/Digital Signal Processor (DSP) 58, and a memory 60 storing code for execution by the microcontroller/DSP, and I/O interface 59 for connection to a personal computer which is used as a test port for running system diagnostics, base unit software upgrades, etc., and a user interface 61. The user interface 61 may consist of the following: a display for indicating electrode programming information or error/alarm conditions, a keypad or buttons for user requested inputs, an alarm unit for audibly indicating error/alarm conditions (for example a detached, low battery or failed electrode), and LEDs for visually indicating error, alarm or programming status.

The time slot EMG data received from the wireless transceivers is demultiplexed in demultiplexer 62 and supplied to a buffer 64. A digital to analog filter bank 66 converts the multiple channels of digital data from the wireless transceivers to analog form. The analog signals are amplified by amplifiers 68 and supplied to an OEM (original equipment manufacturer) standard EMG monitor interface 70. The interface 70 could be either part of the base unit 18 assembly so that it can directly plug into the EMG display equipment 14 via a standard connector, or it could be part of a cable connection to the display equipment. The idea with the OEM interface 70 is to supply multiple analog EMG signals to the conventional EMG display equipment already used in the hospital environment, in a compatible and transparent manner, such that the display equipment would treat the signals as if they were generated from conventional wired electrodes. Familiarity with the analog signal acquisition hardware or electronics for the EMG display equipment 14 will be required obviously, and the OEM interface circuitry may vary depending on the manufacturer of the display equipment. The OEM monitor interface detailed design is considered within the ability of a person skilled in the art.

Referring to FIG. 10, a possible transmission scheme between the wireless transceivers 20 and the base unit 18 is time division multiplexing. This allows a single transmit frequency to be used by all the electrodes in the EMG system. All electrodes receive commands and synchronization data (time base signal, reference signal and control data 76) from the base unit 18 on an assigned receive frequency (downlink) channel. The electrode receive channel may or may not be slotted (time multiplexed). Electrode #1 20 transmits it's data on time slot 1 (72), electrode #2 on time slot 2 (74), etc. at the assigned transmit frequency (uplink) channel. The base unit 18 receives the transmission from the electrodes and demultiplexes, buffers, and reconstructs the individual electrode data.

The system 10 of FIG. 1 utilizes an over the air programming mechanism to exchange messaging and information between the base unit 18 and the wireless transceivers 20. Various types of information could be exchanged. For example, the base unit 18 transmits a data acquisition control message to the wireless transceivers, which tells the microcontroller in the wireless transceivers to start and stop data acquisition. Another command would be a frequency selection command message sent to the wireless transceivers, in which the wireless transceivers responsively select a common frequency channel for transmission of acquired EMG signals to the base unit in discrete time slots.

The following is a list of some of the possible programming commands and messages that could be sent between the base unit and the wireless transceivers:

a. Registration of electrodes with the base unit 18. This would include the detection of the electrode type and an associated unique electrode identifier by the base unit. This could also include transmission of a unique base unit identifier to the electrodes (for example where multiple base units are within RF range of the electrodes) and detection of the base unit identifier by the electrode. Also, a patient reference number could also be stored in each electrode so it only receives commands from a specific patient-assigned base unit. Each electrode reference number is also stored in the base unit, so that data coming only from these electrodes is accepted. An additional registration feature would be assignment of a specific electrode function (i.e., position on the patient's body). With each of the above commands and messages, the receiving unit would typically transmit back an acknowledgment signal indicating the receipt of the command and sending back any required information to the transmitting unit.

b. Configuration of data acquisition sampling rate.
c. Configuration of amplifier 30 gain setting.
d. Configuration of preamplifier filter band settings.
e. Configuration of carrier channel settings, namely the frequency of the carrier signal generated by the frequency generator 46 in the transceivers.
f. Configuration of timing signal for transmission time slot. This needs to be synchronized with the data acquisition rate.
g. Battery 45 utilization sleep/activation mode.
h. Battery 45 low voltage level detection.
i. Data acquisition start/stop scenario.
j. Data transmit procedure.
k. Error sample data recover/retransmit scenario.
l. System test diagnostic procedure
m. Scan of electrode current channel setting procedure
n. Electrode detection procedure.
o. Electrode status audit.
p. Base unit status audit.
q. Data acquisition subsystem audit.

Further details on initialization and over the air programming techniques for a wireless sensors are described in greater detail in the patent applications of Mohammed Khair et al., Ser. No. 09/551,718 and Ser. No. 09/551,719, both filed on filed Apr. 18, 2000, which are incorporated by reference herein.

Persons skilled in the art will appreciate that the details of the presently preferred embodiment described herein can be changed and modified without departure from the spirit and scope of the invention. The system can be used to acquire ECG signals, electroencephalogram signals, electromyography signals, or other types of signals. This true spirit and scope is to be determined in reference to the appended claims.

We claim:

1. A wireless biopotential sensor, comprising:

an adhesive strip having a lower surface for placement against the skin of a patient and an upper surface;

a pair of conductive electrodes applied to said adhesive strip for detecting biopotential signals, the conductive electrodes comprising elongate strips of conductive material wrapped around said adhesive strip and separated from each other by a distance;

a sensor substrate applied to said upper surface of said adhesive strip, said sensor substrate carrying first and second conductive contact pads placed in registry with said pair of conductive electrodes such that said contact pads are in electrical contact with said conductive electrodes;

an electronics module applied to said sensor substrate and in electrical contact with said contact pads, said electronics module comprising a power supply and electronics for generating a wireless signal containing biopotential signals detected by said pair of conductive electrodes.

2. The sensor of claim 1, wherein said adhesive strip comprises a flexible, double sided adhesive tape.

3. Ta sensor of claim 1, further comprising a flexible protective tape applied to said lower surface of said adhesive strip.

4. The sensor of claim 1, further comprising a flexible strip attached to said sensor module and a reference vol age electrode supplying a reference voltage to said electronics module, said reference voltage electrode being positioned at the end of said flexible strip.

5. T e sensor of claim 4, wherein said flexible strip further comprises an adhesive material for connecting said end of said flexible strip to the patient.

6. T e sensor of claim 1, wherein said sensor is adapted for measuring an electromyography signal from a human patient.

7. An electromyography signal acquisition system comprising a plurality of bio-potential sensors as recited in claim 1, wherein said electronics module transmits said wireless signals, and further comprising a base unit for receiving said wireless signals from said bio-potential sensors.

8. The sensor of claim 1, further comprising DIP switch for enabling a user of said sensor to select an identification number for said sensor, wherein the identification number selected by said user with said DIP switch is encoded with said wireless signal by said electronics module.

* * * * *